United States Patent [19]
Bollinger et al.

[11] Patent Number: 6,024,725
[45] Date of Patent: Feb. 15, 2000

[54] REDUCING TISSUE TRAUMA AND FLUID LOSS DURING SURGERY

[75] Inventors: Stephen A. Bollinger, Carpinteria, Calif.; Robert L. Guest, Bedford, Tex.; John T. Garibotto, Newark, Calif.

[73] Assignee: Mentor Corporation, Santa Barbara, Calif.

[21] Appl. No.: 08/756,381

[22] Filed: Nov. 27, 1996

[51] Int. Cl.[7] .................................................. A61M 5/00
[52] U.S. Cl. ........................................... 604/164; 604/264
[58] Field of Search ...................................... 604/117, 158, 604/164, 167, 169, 170, 171, 174, 175, 264

[56] References Cited

U.S. PATENT DOCUMENTS

| | | |
|---|---|---|
| 3,589,363 | 6/1971 | Banko . |
| 3,805,787 | 4/1974 | Banko . |
| 3,956,826 | 5/1976 | Perdreaux, Jr. . |
| 3,990,452 | 11/1976 | Murry et al. . |
| 4,000,739 | 1/1977 | Stevens . |
| 4,040,414 | 8/1977 | Suroff . |
| 4,136,700 | 1/1979 | Broadwin et al. . |
| 4,223,676 | 9/1980 | Wuchinich et al. . |
| 4,425,115 | 1/1984 | Wuchinich . |
| 4,526,571 | 7/1985 | Wuchinich . |
| 4,634,419 | 1/1987 | Kreizman et al. . |
| 4,655,752 | 4/1987 | Honkanen et al. . |
| 4,735,605 | 4/1988 | Swartz . |
| 4,792,327 | 12/1988 | Swartz . |
| 4,808,154 | 2/1989 | Freeman . |
| 4,815,462 | 3/1989 | Clark . |
| 4,886,491 | 12/1989 | Parisi et al. . |
| 4,920,954 | 5/1990 | Alliger et al. . |
| 4,922,902 | 5/1990 | Wuchinich et al. . |
| 4,989,588 | 2/1991 | Kubota et al. . |
| 4,994,042 | 2/1991 | Vadher . |
| 5,009,643 | 4/1991 | Reich et al. . |
| 5,026,387 | 6/1991 | Thomas . |
| 5,069,664 | 12/1991 | Guess et al. . |
| 5,112,300 | 5/1992 | Ureche . |
| 5,123,903 | 6/1992 | Quaid et al. . |
| 5,151,084 | 9/1992 | Khek . |
| 5,151,085 | 9/1992 | Sakurai et al. . |
| 5,209,719 | 5/1993 | Baruch et al. . |
| 5,211,647 | 5/1993 | Schmieding . |
| 5,222,937 | 6/1993 | Kagawa . |
| 5,226,890 | 7/1993 | Ianniruberto et al. . |
| 5,236,414 | 8/1993 | Takasu . |
| 5,248,298 | 9/1993 | Bedi et al. . |
| 5,273,545 | 12/1993 | Hunt et al. . |
| 5,279,547 | 1/1994 | Costin . |
| 5,282,820 | 2/1994 | Goodstein . |
| 5,300,035 | 4/1994 | Clement . |
| 5,324,268 | 6/1994 | Yoon . |
| 5,336,176 | 8/1994 | Yoon . |
| 5,364,372 | 11/1994 | Danks et al. ............................ 604/264 |
| 5,419,761 | 5/1995 | Narayanan et al. . |
| 5,445,617 | 8/1995 | Yoon . |
| 5,545,150 | 8/1996 | Danks et al. ............................ 604/167 |
| 5,556,411 | 9/1996 | Taoda et al. ............................ 604/164 |
| 5,591,191 | 1/1997 | Kieturakis ............................... 604/164 |
| 5,651,773 | 7/1997 | Perry et al. ............................. 604/174 |
| 5,662,673 | 9/1997 | Kieturakis ............................... 604/264 |

*Primary Examiner*—Wynn Wood Coggins
*Assistant Examiner*—Deborah Blyveis
*Attorney, Agent, or Firm*—Fish & Richardson P.C.

[57] ABSTRACT

A sleeve for introducing a surgical instrument (e.g., a lipoplasty probe) into the body via a wound pierced in the skin, and an insertion device for making the wound and inserting the sleeve therethrough are provided. The sleeve reduces the transmission of friction and heat (e.g., caused by the highly repetitive in-and-out and rotational movements and ultrasonic vibration of the lipoplasty probe) to the skin of the patient. In addition, the size of the hole associated with insertion of the sleeve is significantly smaller and more uniform in shape than that associated with a traditional scalpel incision. By piercing the skin, rather than making an incision with a scalpel, and by reducing friction and heat transmission to the skin, the irritation, inflammation, flowering (i.e., curling up of the skin at the edges of an incision), and scarring associated with lipoplasty are minimized, and the cosmetic result of the procedure is improved.

32 Claims, 10 Drawing Sheets

REDUCING TISSUE TRAUMA AND FLUID LOSS DURING SURGERY

BACKGROUND OF THE INVENTION

This invention relates to a sleeve through which a surgical instrument (such as a lipoplasty probe) is inserted into a patient for reducing tissue trauma and fluid loss during surgery, and a device for introducing the sleeve through the skin.

The surgical technique of lipoplasty involves removing unwanted fatty deposits by separating the fat from surrounding tissue and aspirating the fat through a probe. Typically, the probe is inserted through an incision made in the patient's skin into a region of fat located between the skin and the underlying muscle. Some lipoplasty probes are simply manipulated by hand (e.g., using a back-and-forth, thrusting motion) to separate the fat. Other lipoplasty probes are ultrasonically vibrated to create localized tissue separation and frictional heating within the fatty region to melt at least some of the fat and facilitate the fat removal. This latter lipoplasty technique is known as ultrasonically-assisted lipoplasty, or "UAL".

Typically, irrigating fluid is introduced into the fatty region to magnify and separate fat from the surrounding tissues, and to facilitate aspiration of the fat through the probe. The irrigating fluid is usually saline, but other ingredients (such as anesthetics, antibiotics, vasoconstrictors, and/or coagulants) may be added to improve patient comfort, reduce blood loss, and reduce the risk of infection or other complications. Some lipoplasty probes include an outer sheath through which the irrigating fluid is conveyed to the surgical site. Alternatively, in a technique known as "tumescence," large amounts of irrigating fluid are injected into the fatty region prior to (and during) the lipoplasty procedure.

SUMMARY OF THE INVENTION

One general aspect of the invention features a sleeve for a surgical instrument. The sleeve includes a hollow tube having a passage sized to accommodate the surgical instrument and extending between a proximal region of the tube and a distal region of the tube, a seal for the surgical instrument disposed within the passage, threads disposed on an exterior surface of the tube for engaging the skin, and an element disposed at the proximal region of the tube and configured to be engaged by a corresponding element of a tool to transmit torque from the tool to the tube, thereby to allow the tool to rotatably advance the tube into the skin using the threads.

Preferred embodiments may include one or more of the following features.

The element is a radially oriented slot disposed in a proximal surface of the tube and configured to receive a corresponding protrusion on the tool. Preferably, a plurality of circumferentially spaced, radially oriented slots are provided on the proximal surface for receiving a corresponding plurality of protrusions on the tool. The proximal surface is disposed on a cap attached to the proximal region of the tube.

The cap engages an interior portion of a tube wall the proximal end of which surrounds the passage. The interior portion of the wall is notched, and the cap includes a resilient projection configured to be received by the notch to provide a snap fit between the cap and the tube. Preferably, the notch is disposed around the perimeter of the interior surface, and the cap includes a plurality of circumferentially spaced, resilient tabs each of which includes the projection.

The wall is a proximal extension of the tube, and flares radially outwardly from the tube so that the proximal end of the wall is radially spaced from the exterior surface of the tube and disposed proximally of a proximal end of the tube. The cap includes an annular neck disposed adjacent the proximal end of the tube when the cap is attached to the tube. When the cap is attached to the tube, the seal is captured between the annular neck of the cap and the proximal end of the tube. Preferably, the tube and the wall comprise an integral unit made from a single piece of plastic material.

The cap and the proximal region of the tube include gripping projections. The cap includes an opening through which the surgical instrument is inserted into the tube passage. The seal is annular and has an opening sized to receive the surgical instrument via the cap opening while maintaining surrounding portions of the seal in contact with the surgical instrument. The seal preferably is a silicone gasket. A plug is insertable into the cap opening to close the proximal end of the passage. The sleeve, cap, and plug preferably are single-use, disposable items.

Another general aspect of the invention features a device for inserting a sleeve for a surgical instrument into a patient. The device includes a handle, a post extending from an end of the handle and configured to receive the sleeve, and an element disposed on the end of the handle and configured to engage a corresponding element on the sleeve to transmit torque from the handle to the sleeve, thereby to allow the handle to rotatably advance the sleeve into the skin. The insertion device also includes a stylet slidably disposed within the post and movable between a retracted position in which a sharp tip of the stylet is disposed within the post, and an extended position in which the tip protrudes from the post for piercing the skin to create an opening for the post and sleeve.

Preferred embodiments may include one or more of the following features.

A spring is disposed within the handle and coupled to the stylet for biasing the stylet to the retracted position. A pin, coupled to the stylet and protruding through an opening in the handle, is movable within the opening to move the stylet between the retracted position and the extended position. The opening includes a portion arranged along a longitudinal axis of the handle and a portion arranged transversely to the axis. The pin is movable within the axial portion of the opening to move the stylet between the retracted position and the extended position, and is displaceable into the transverse portion of the opening to maintain the stylet in the extended position.

The sleeve used with the insertion device may include any of the features discussed herein.

Other aspects of the invention feature an assembly that includes the sleeve and the insertion device, and methods of using the same.

Among other advantages, the sleeve and insertion device are easy to use. The user inserts the sleeve onto the post of the insertion device so that the torque-transmitting element disposed on the end of the handle engages the corresponding element on the sleeve. The stylet is advanced through the hollow post and used to pierce the skin, and is then retracted into the post. Next, the user rotates the handle to rotatably advance the sleeve into the skin using the threads. When the sleeve is fully inserted, the handle is disengaged from the sleeve and withdrawn. Thereafter, a surgical instrument (such as an ultrasonic lipoplasty probe) is inserted into the body through the sleeve.

The sleeve reduces the transmission of friction and heat (e.g., caused by the highly repetitive in-and-out and rotational movements of the lipoplasty probe) to the skin of the patient. By reducing friction and heat transmission to the skin, the resultant irritation, inflammation, and flowering (i.e., curling up of the skin at the edges of an incision) which may occur at the incision site are diminished, and the cosmetic result of the procedure is improved.

In addition, the size of the wound associated with insertion of the sleeve is significantly smaller than that associated with a traditional scalpel incision. By piercing and dilating the skin with the insertion device and the sleeve, rather than making a free-hand incision with a scalpel, scarring is minimized, healing time is reduced, and the cosmetic result is improved. Moreover, because the sleeve is threadably advanced into the wound, the hole pierced in the patient's skin can be quite small in size.

The exterior threads on the sleeve tightly engage the patient's skin to resist displacement from the patient's skin and help avoid the loss of fluid from the patient around the sleeve. The threaded tube is larger in diameter than the hole pierced in the skin by the insertion device. Therefore, the threaded nature of the sleeve, the smaller diameter of the hole, and the skin's inherent resiliency combine to create a secure and fluid-tight interface between the sleeve and the skin.

The interior seal forms a fluid-tight seal around the surgical instrument, thereby reducing fluid loss through the sleeve passage during surgery. When the sleeve is used with an ultrasonic lipoplasty instrument, the seal also reduces the aerosolization of fluids by the ultrasonically vibrating probe by wiping fluids from the probe as the user removes the probe from the patient. Reduced aerosolization helps maintain aseptic technique and diminishes the health risks of operating room personnel during the procedure.

Following removal of the probe, the plug is inserted into the sleeve to close the passage and prevent unwanted fluid loss from the surgical site. The ability to close the sleeve is particularly important when performing tumescent lipoplasty, in which large quantities of irrigating fluid (e.g., saline containing anesthetics, antibiotics, vasoconstrictors, and/or coagulants) are injected into the area of fatty tissue prior to and during surgery. The large volume of irrigating fluid or tumescing fluid induces a relatively large hydrostatic pressure gradient from inside to outside the patient. Thus, closing the sleeve with the plug avoids potentially significant fluid loss.

The insertion device, like the sleeve, is preferably a single-use disposable item. The stylet pin is readily accessible, and the configuration of the spring-loaded stylet and the handle opening allows the user to extend and retract the stylet with the thumb of one hand. Because the stylet is retractable, the sleeve may be loaded onto the hollow post of the insertion device without damaging (e.g., cutting) the seal. The retractable stylet also enhances patient and operating room personnel safety during use. In addition, dilation of the hole pierced in the patient's skin, and the resulting tight fit of the sleeve, is facilitated by a series of tapered steps created by the sharpened stylet tip, the tapered end of the hollow post of the insertion device, and the tapered end of the sleeve.

Other features and advantages of the invention will become apparent from the following detailed description, and from the claims.

BRIEF DESCRIPTION OF THE DRAWINGS

FIG. 8 shows the plug of FIG. 7 in use.

DESCRIPTION OF PREFERRED EMBODIMENTS

Figure 1:
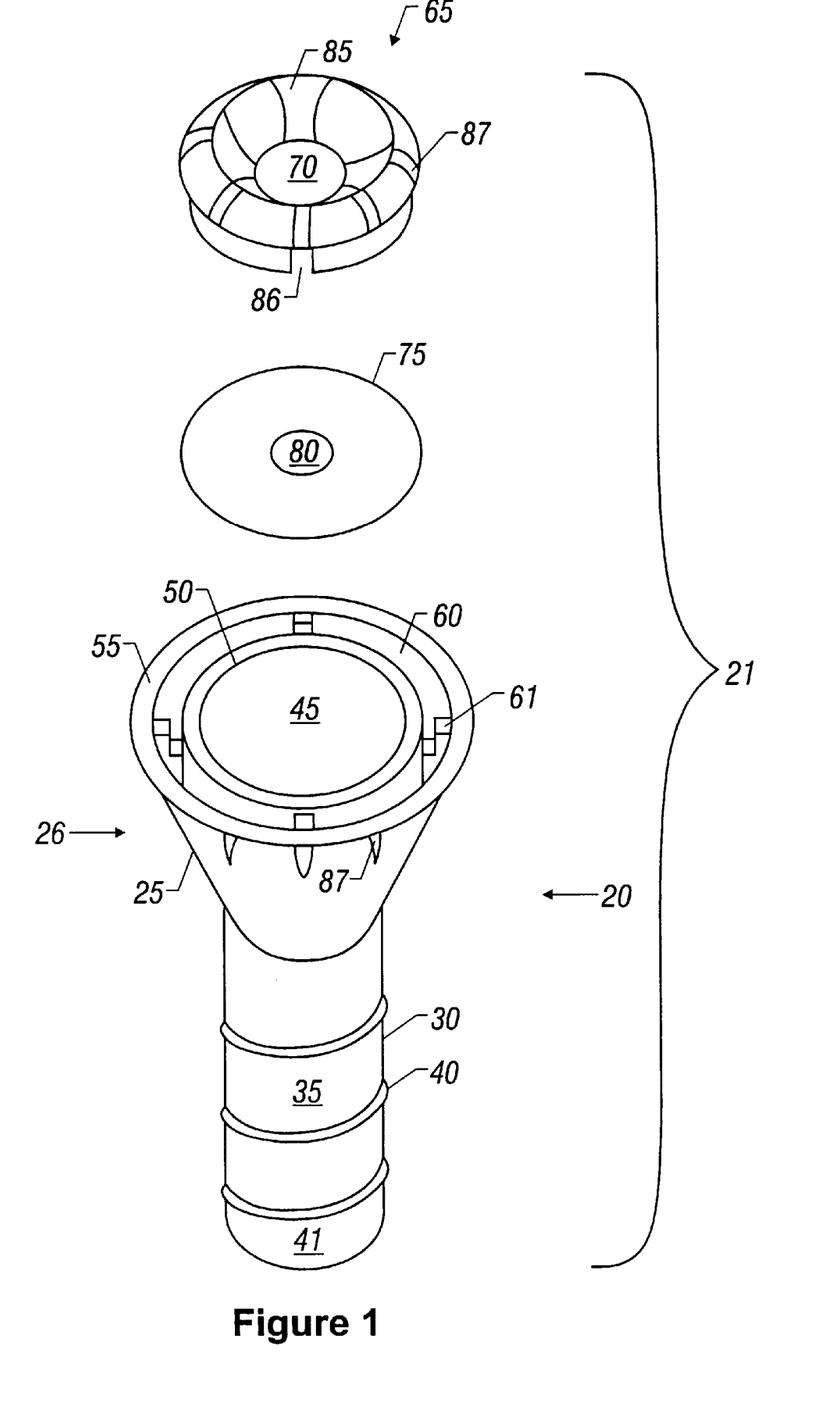
FIG. 1 is an exploded view of a sleeve used during lipoplasty surgery.
Figure 2:
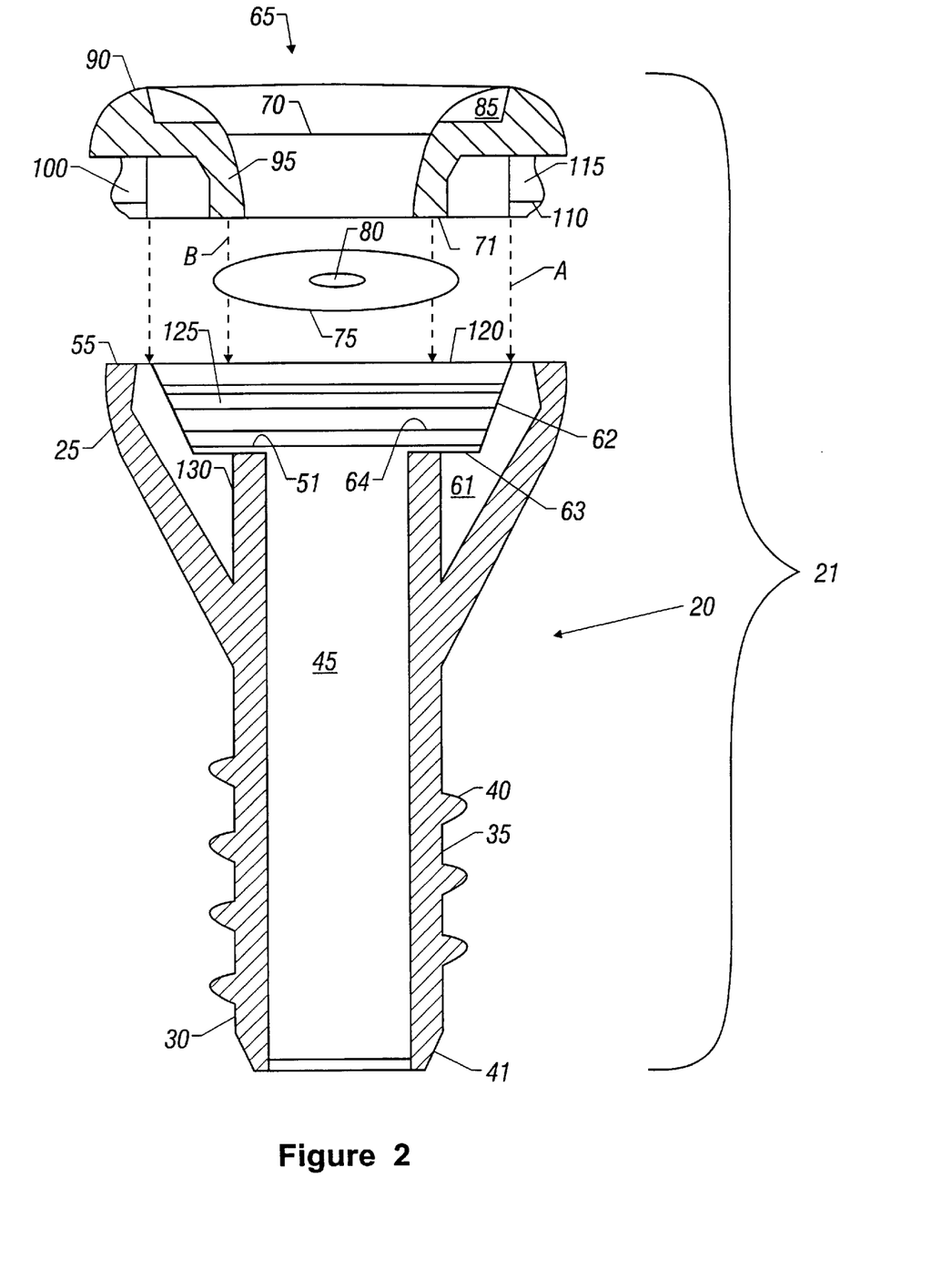
FIG. 2 is a cross-sectional view of the sleeve of FIG. 1.
Figure 5A:
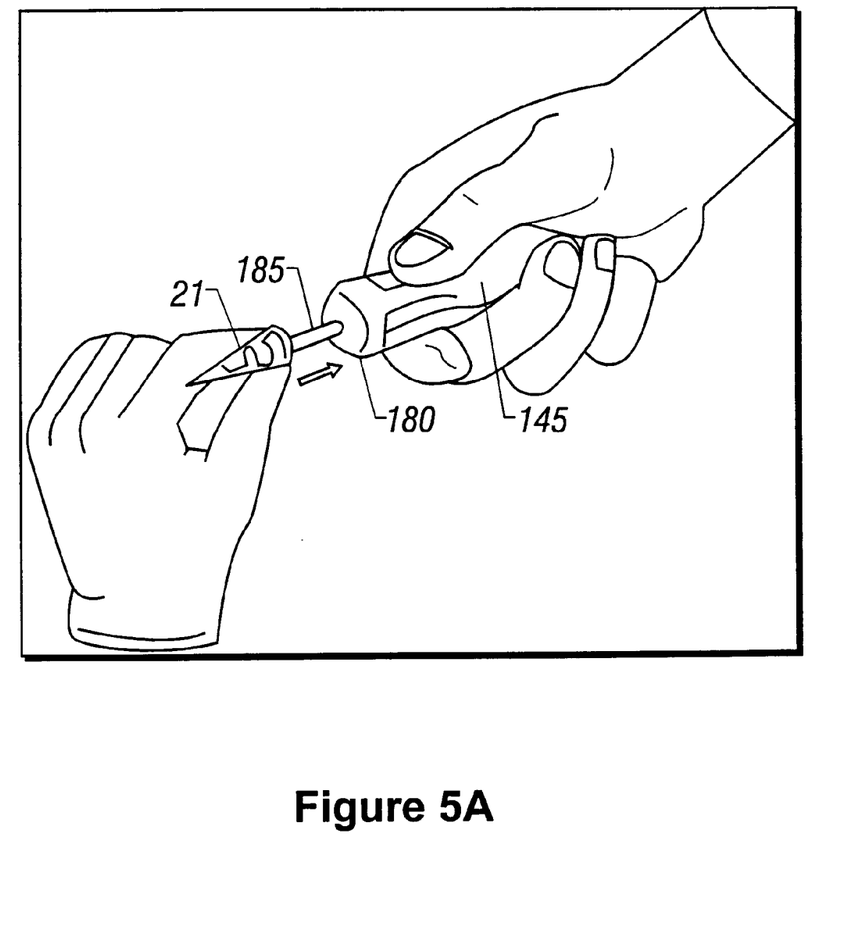
FIGS. 5A–5E show the sleeve and trocar of FIGS. 1 and 3 in use.
Figure 5B:
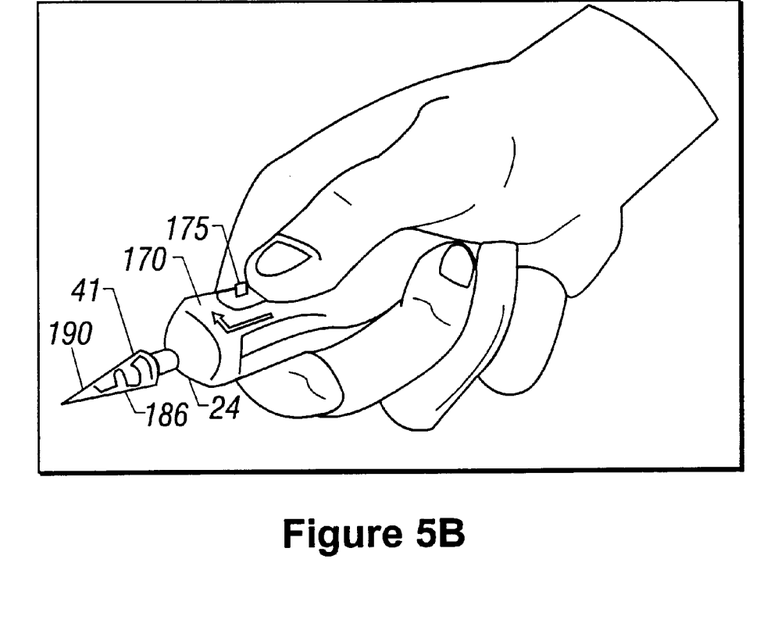

Referring to FIGS. 1 and 2, sleeve 21 for use during surgery (e.g., lipoplasty) includes threaded tube 20 within which a seal 75 (e.g., a silicone wiper gasket) is secured by cap 65 which snap fits onto threaded tube 20. Cap 65 includes notches 85 which are engageable by corresponding prongs 180 of trocar 145 (see FIGS. 5B and 5C) to allow trocar 145 to transmit torque to sleeve 21 and threadably advance sleeve 21 into the skin of a patient. Threaded tube 20 and cap 65 are made from plastic and are easily assembled together to capture seal 75, and thus, sleeve 21 is economically disposable after a single use.

Threaded tube 20 includes an open-ended, flared head 25 at its proximal end 26 from which hollow elongated shaft 30 extends to open distal end 41. A passage 45 passes completely through head 25 and shaft 30 and has a diameter sized to receive a surgical instrument (e.g., a lipoplasty probe, not shown). Exterior surface 35 of shaft 30 includes threads 40 for securing threaded tube 20 within a hole pierced in the skin of a patient, as discussed below. Distal end 41 of shaft 30 is bevelled (FIG. 2) to facilitate insertion into the patient's skin through the hole. Passage 45 is surrounded by tubular wall 50 which extends proximally into head 25 and terminates in annular shoulder 51 which is recessed from annular proximal end 55 of head 25. Annular shoulder 51 is radially spaced from annular proximal end 55 by gap 60 across which L-shaped support spokes 61 extend (see FIG. 1).

Cap 65 engages head 25 and secures seal 75 between cap 65 and head 25. Cap 65 includes central aperture 70 which extends downwardly and is circumscribed by neck 71. Cap 65 also includes grooves 86 (FIG. 1) which receive spokes 61 upon engagement of cap 65 with threaded tube 20. Seal 75 includes central opening 80 which is somewhat smaller in diameter than the diameter of the surgical instrument for purposes to be described.

Figure 3:
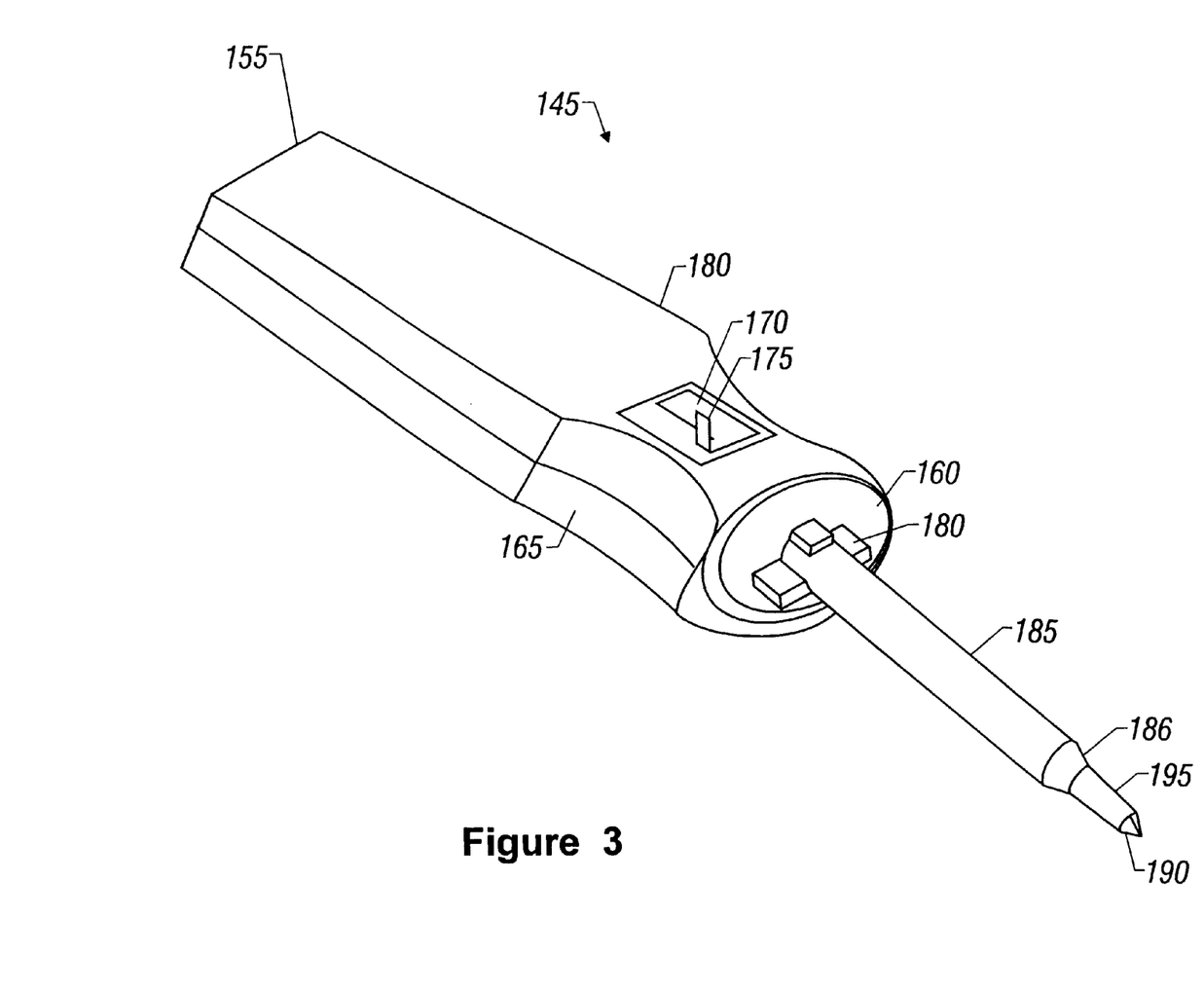
FIG. 3 shows a trocar for inserting the sleeve of FIG. 1 into the body.

Cap 65 also includes notches 85 which provide a keying mechanism for engaging a reciprocal set of prongs on trocar 145 used to insert sleeve 21 into the patient (see FIG. 3). The keying mechanism allows the surgeon to advance sleeve 21 into the skin using trocar 145 in a manner similar to a screwdriver. For further ease of use, the exterior surfaces of cap 65 and threaded tube 20 include gripping projections 87 which extend from outer annular wall 100 and upper arcuate surface 90, respectively. Gripping projections 87 facilitate removal by the surgeon's hands of assembled sleeve 21 from the patient following lipoplasty.

Cap 65 includes upper arcuate surface 90 from which inner and outer annular walls 95, 100 extend downwardly. Inner annular wall 95 is radially-spaced apart from outer annular wall 100. Outer annular wall 100 is separated into tabbed sections by four grooves 86 (see FIG. 1). Each tabbed section includes a tooth 110 projecting circumferentially from its exterior surface 115. Interior surface 120 of exterior annular wall 55 of head 25 includes circumferential groove 125 sized to receive teeth 110. Upper vertical portion 62 of L-shaped support spokes 61 extends from interior surface 120 via lower horizontal portion 63 to meet exterior surface 130 of tubular wall 50. Annular shoulder 51 and lower horizontal portion 63 combine to form a platform 64 which supports seal 75 when cap 65 and threaded tube 20 are engaged.

As shown by the dashed lines A and B, seal 75 is secured between cap 65 and threaded shaft 20 by inserting outer annular wall 100 of cap 65 within head 55. Insertion is accomplished by aligning grooves 86 with upper vertical portion 62 and compressing cap 65 into head 55 of threaded tube 20. Once inserted, teeth 110 "snap fit" within groove 125, and seal 75 is captured between neck 71 and platform 64. Rotation of cap 65 about head 25 during insertion of sleeve 21 with trocar 145 (see FIG. 3) is prevented by the engagement of grooves 86 of cap 65 and spokes 61 of head 25.

Threaded tube 20 is approximately 1 inch in length, with head 25 and shaft 30 being approximately 0.45 inch and 0.055 inch in length, respectively. Of the approximate 0.55 inch length of shaft 30, approximately 0.45 inch is threaded. The threads of shaft 30 have a pitch of approximately 0.10 inch, a thickness of approximately 0.035 inch, and extend from exterior surface 35 of shaft 30 of threaded tube 20 approximately 0.05 inch. Head 25 and tubular wall 50 of threaded tube 20 have an outer diameter of approximately 0.625 inch and 0.310 inch and a thickness of approximately 0.025 inch and 0.070 inch, respectively. Cap 65 has a height of approximately 0.20 inch and a width of approximately 0.70 inch. Inner and outer annular walls 95, 100 of cap 65 have an outer diameter of approximately 0.325 and 0.565 inch and a thickness of approximately 0.10 and 0.05 inch, respectively. The outer diameter of tooth 110 is approximately 0.825 inch. Cap 65 and threaded tube 20 are single-use disposable items made from plastic.

Referring to FIG. 3, a trocar 145 for inserting sleeve 21 into a patient includes handle 150 having proximal end 155 and distal end 160. Handle 150 is tapered in thickness near proximal end 155, and includes a pair of contoured grips 165 near distal end 160. Hollow post 185, onto which sleeve 21 is inserted, extends from distal end 160 of trocar 145. Post 185 is slightly longer than sleeve 21 so that, with sleeve 21 in place on post 185, bevelled tip 186 of post 185 protrudes slightly beyond bevelled tip 41 of sleeve 21. Four radially-spaced prongs 180 are positioned on distal end 160 of the trocar to provide a keying mechanism for engaging notches 85 of cap 65 of sleeve 21 (see FIGS. 1 and 2).

Spring-loaded stylet 195 is retractably positioned within hollow post 185. Pin 175 mounted at the proximal end of stylet 195 extends through J-shaped slot 170 in handle 150 for use by the surgeon in moving stylet 190 between a retracted position (in which sharpened tip 190 of stylet 195 is disposed within post 185) and an extended position. In the extended position (shown in FIGS. 3 and 4B), sharpened tip 190 extends beyond bevelled tip 156 of hollow post 185 for use in piercing the skin. Sharpened tip 190 of stylet 195, bevelled tip 186 of hollow post 185, and bevelled tip 41 of sleeve 21 combine to provide a series of tapered steps (see FIG. 5B). Sharpened tip 190, bevelled tip 186, and bevelled tip 41 (i.e., the tapered portions) are separated by small segments of stylet 195, hollow post 185, and sleeve 21 which have a constant diameter (i.e., provide a short plateau between each tapered portion). The tapered steps allow the small hole, pierced in the patient's skin with sharpened tip 190 of stylet 195, to be progressively dilated as sleeve 21 is advanced.

Figure 4A:
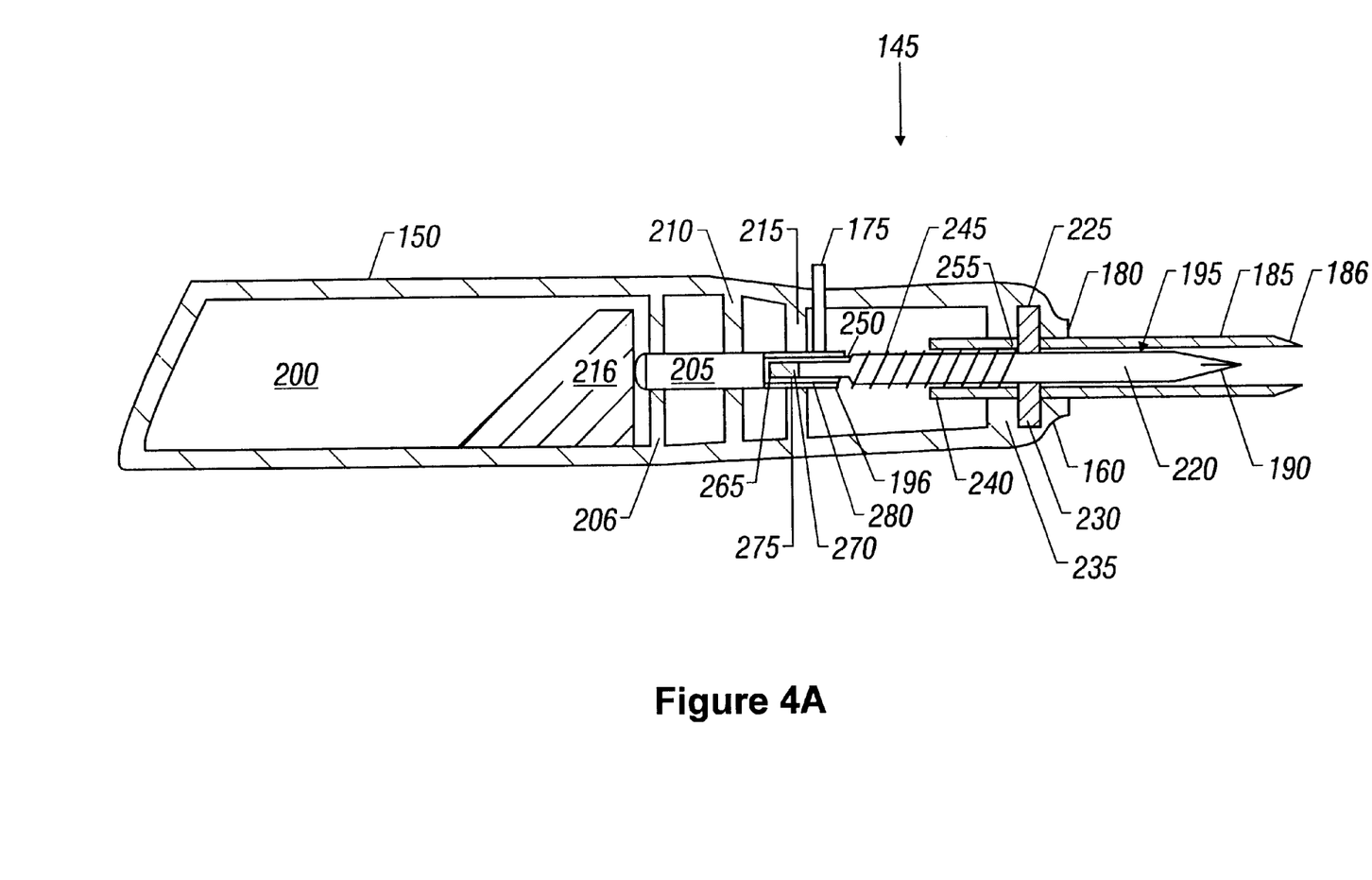
FIGS. 4A and 4B are cross-sectional views of the trocar of FIG. 3 which respectively show a spring-loaded stylet in a retracted position and an extended position.

Referring to FIG. 4A, handle 150 of trocar 145 is substantially hollow, and defines interior cavity 200. Stylet 195 is disposed within interior cavity 200, and includes stylet body 205 from which stylet pin 175 extends at a right angle to exit handle 150 through J-shaped slot 170. Stylet body 205 and pin 175 are molded as single piece of plastic. The position of stylet body 205 within interior cavity 200 is maintained by a series of spaced support struts 206, 210, 215. The proximal displacement of stylet body 205 is limited by stylet stop 216, positioned proximal to support struts 206, 210, 215. Metal stylet shaft 220, inserted into chamber 280 within the stylet body, extends from shoulder 196 of stylet body 205, and terminates at sharpened tip 190. The proximal end of stylet shaft 220 has knurled surface 270 for frictionally engaging stylet body 205 at proximal end 275 of chamber 280.

The proximal end of hollow post 185 is secured within interior cavity 200 by the engagement of flange 225 within flange slot 230 in the distal end 160 of handle 150. Flange slot 230 is bounded on one side by interior surface 161 of distal end 160 of handle 150 and on the other side by collar support 235. Collar 240 extends proximally from flange 225 and protrudes into interior cavity 200 to encircle the distal end 255 of a compression spring 245. The proximal end 250 of spring 245 abuts shoulder 196 of stylet 195, while distal end 255 of spring 245 abuts flange 225 of hollow post 185.

All components of trocar 145 (with the exception of stylet shaft 220 and compression spring 245) are made entirely of plastic. Trocar 145 thus is economically disposable after a single-use.

When stylet pin 175 is at the proximal end of J-shaped slot 170 (see FIGS. 3 and 4A), stylet tip 190 is retracted within hollow post 185 by the expansion of compression spring 245. In general, stylet tip 190 is retracted when trocar 145 is not in use, or after the surgeon has pierced the skin and is prepared to advance sleeve 21 into the skin with trocar 145.

Figure 4B:
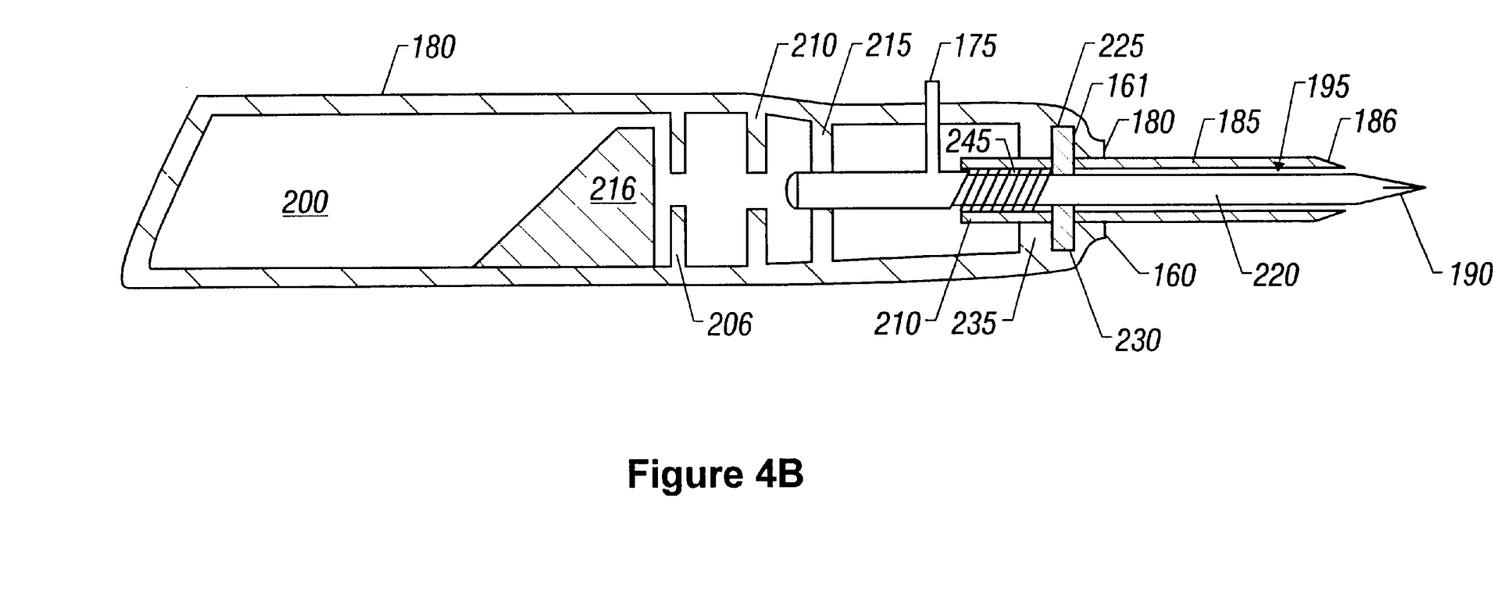

FIG. 4B shows stylet 195 in the extended position in which sharpened tip 190 extends beyond bevelled tip 186 of hollow post 185. The surgeon advances stylet 195 by placing his or her thumb adjacent stylet pin 175 and sliding pin 175 distally within J-shaped slot 170 to compress spring 245. The extended position of stylet 195 may be maintained by either manually holding stylet pin 175 in the distally-advanced position or by laterally displacing stylet pin 175 so as to engage stylet pin 175 in the hook-shaped portion of J-shaped slot 170 (FIG. 3). Once the surgeon has pierced the skin with sharpened tip 190, stylet pin 175 may be disengaged from the hook-shaped portion of J-shaped slot 170, allowing compression spring 245 to expand, and thereby retract sharpened tip 190 into hollow post 185.

Referring to FIGS. 5A–5E, in use, sleeve 21 is advanced over hollow post 185 of trocar 145 (in the direction of the arrow in FIG. 5A) so that hollow post 185 fits snugly within opening 80 of seal 75. Prongs 180 of trocar 145 are aligned with and inserted into notches 85 of cap 65. Sharpened tip 190 of stylet 195 is then extended beyond bevelled tip 260 of hollow post 185 by advancing stylet pin 175 (e.g., with the surgeon's thumb) first distally and then laterally to engage it in the hook-shaped portion of J-shaped slot 170 (as shown by the arrow in FIG. 5B). Trocar 145 is now ready to pierce the skin.

Figure 5C:
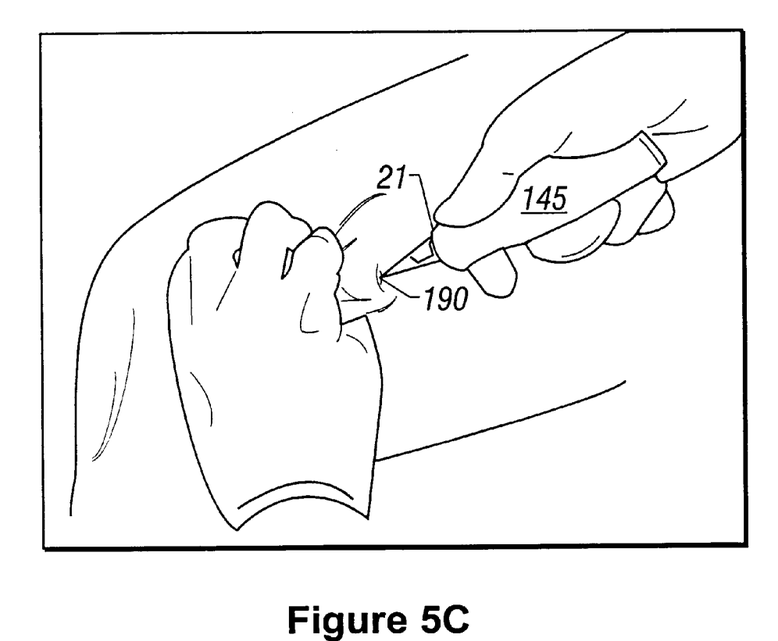
Figure 5D:
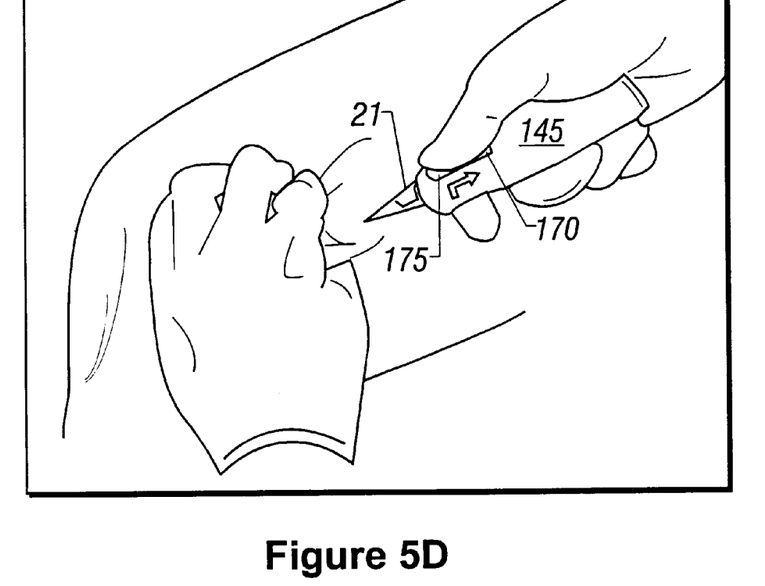
Figure 5E:
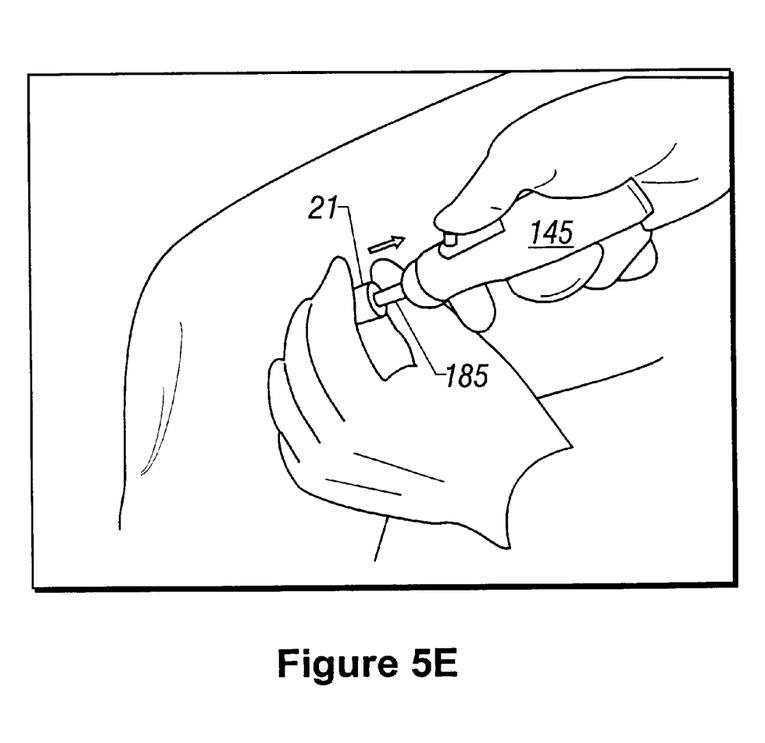

Using one hand, the surgeon positions sharpened tip 190 over the patient's skin at a selected site (e.g., proximal to the patient's knee on the front of the thigh), and using the other hand, the surgeon grasps the skin between his or her thumb and forefinger to elevate the site to be pierced from the underlying tissue (FIG. 5C). The surgeon then pierces the skin with sharpened tip 190. Sharpened tip 190 is then retracted into hollow post 185 by displacing stylet pin 175 laterally to disengage it from the hook-shaped portion of J-shaped slot 170. The surgeon then removes his or her thumb from stylet pin 175 so that compression spring 245 may expand and proximally displace stylet pin 175 within slot 170 and retract sharpened tip 190 within hollow post 185 (as shown by the arrow in FIG. 5D). Sleeve 21 may then be safely advanced into the skin by rotating trocar 145 (e.g., as one would advance a screw with a screwdriver). Once sleeve 21 is securely in place, hollow post 185 is removed by the surgeon from passage 45 with one hand while grasping sleeve 21 with the opposite hand (see FIG. 5E). Trocar 145 may then be used in inserting other sleeves 21.

Figure 6:
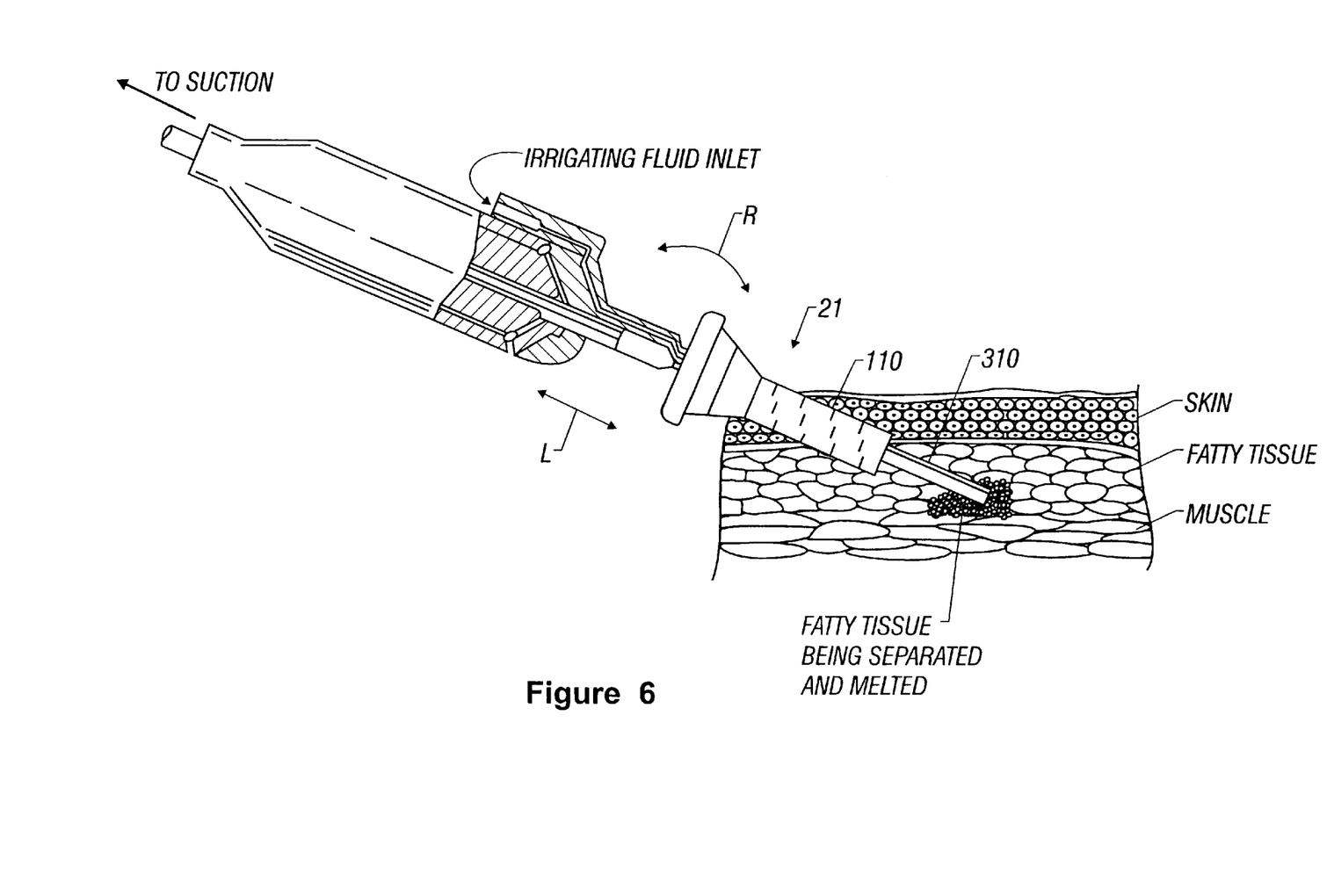
FIG. 6 shows the sleeve of FIG. 1 in use during lipoplasty.

Referring to FIG. 6, after sleeve 21 has been inserted into the patient, the surgeon may insert any suitable surgical instrument into the surgical site through sleeve 21. One example of such a surgical instrument is an ultrasonically-assisted lipoplasty probe 310 (such as the UAL probe described in U.S. Pat. No. 4,886,491, entitled "Liposuction Procedure with Ultrasonic Probe," which is incorporated by reference herein). The surgeon inserts lipoplasty probe 310 through opening 80 of seal 75 and into sleeve passage 45. As indicated by arrows L and R, lipoplasty involves repetitive longitudinal and rotational movements of ultrasonic probe 310, in addition to the ultrasonic vibration of probe 310 itself. Sleeve 21 protects the patient's skin from the friction and heat associated with the motion and vibration of probe 21. In addition, the hole created by trocar 145 is significantly smaller and more uniform in shape than a free-hand scalpel incision. Thus, the extent of scarring may be reduced and the cosmetic result of the surgery enhanced.

In addition to reducing tissue trauma, seal 75 of sleeve 21 (see FIGS. 1 and 2) and the engagement of threads 40 of sleeve 21 with the patient's skin combine to reduce fluid loss during the procedure. When ultrasonic probe 310 is inserted through central opening 80, seal 75 forms a fluid-tight interface with probe 310 to prevent the loss of fluid from the patient through sleeve passage 45. Fluid loss from around sleeve 21 (i.e., at the interface of exterior surface 35 of sleeve 21 and the patient's skin) is also reduced by the threaded engagement of sleeve 21 with the patient's skin. Because the hole pierced in the patient's skin with sharpened tip 190 of stylet 195 is smaller than the diameter of distal end 30 of sleeve 20, the natural resiliency of the patient's skin causes it to compress tightly around sleeve 21. When combined with the security (i.e., frictional resistance to displacement) afforded by threads 40, a fluid-tight seal between sleeve 21 and the patient's skin is created. A fluid-tight seal is particularly important when performing tumescent ultrasonic lipoplasty where large volumes of irrigating fluid may be used to separate the fat from surrounding tissues and to facilitate aspiration of the fat separated and melted by the ultrasonic vibration of probe 310.

When the surgeon is ready to move to another area of fatty tissue, lipoplasty probe 310 is removed from the patient's body. In addition to limiting fluid loss from passage 45 of sleeve 21 during the procedure, seal 75 wipes lipoplasty probe 310 clean of fluid upon its removal from sleeve 21. In so doing, aerosolization of the irrigating fluid and separated fat (i.e., caused by the ultrasonic vibration of probe 310 outside of the patient's body) is significantly reduced.

Figure 7:
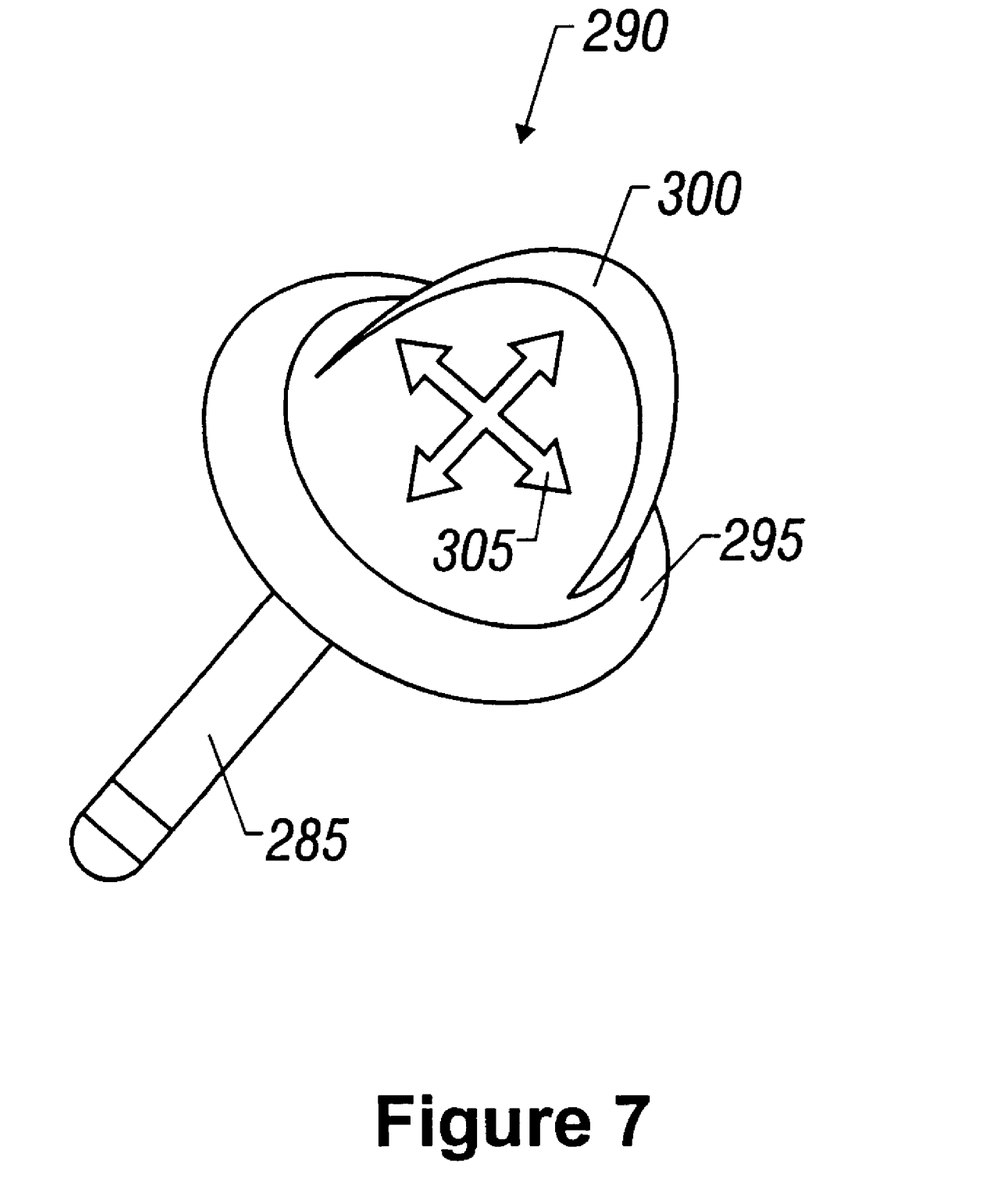
FIG. 7 shows a plug for closing the sleeve of FIG. 1.

Referring to FIGS. 7 and 8, once ultrasonic probe 310 has been removed, sleeve 21 may be closed by inserting stem 285 of sleeve plug 290 into central opening 80 of seal 75. Plug 290 includes platform 295 from which stem 285 extends downwardly and tab 300 extends upwardly. Tab 300 also includes raised surface 305 which enhances the ease of gripping and inserting plug 290 into cap 65 in a wet surgical environment. Plug 290 is made of plastic and is disposable after a single use.

Other embodiments are within the scope of the following claims.

For example, seal 75 may be replaced with other surgically compatible sealing membranes. Alternatively, a single slit, or a plurality of slits (e.g., a Y-shaped or T-shaped slit), may substitute for central opening 80 in seal 75. In another embodiment, outer annular wall 95 of cap 65 snap fits around the outside of exterior annular wall 55 of threaded tube 20 (e.g., like a cap on a bottle). In other embodiments, the keying mechanism can include projections on cap 65 and complementary receptacles on trocar 145. In another embodiment, the keying mechanism includes complimentary surfaces on cap 65 and trocar 145 which frictionally engage upon rotation of trocar 145. In another embodiment, sharpened tip 190 of stylet 195 may be replaced with a cutting blade or other sharpened surface suitable for controlled piercing or slicing of the patient's skin.

Plug 290 may be tethered to either cap 65 or threaded tube 20 of sleeve 21 for additional ease of use (e.g., to prevent having to search for or excessively handle the plug during surgery).

While the invention has been described in terms of lipoplasty surgery (e.g., traditional or ultrasonically-assisted lipoplasty), the invention may also be used with other types of surgeries, for example, plastic surgery, reconstructive surgery, urologic surgery, and other types of endoscopic procedures.

What is claimed is:

1. A sleeve for a surgical instrument, comprising
   a hollow tube having a passage sized to accommodate the surgical instrument and extending between a proximal region of said tube and a distal region of said tube,
   a seal for the surgical instrument disposed within said passage,
   threads disposed on an exterior surface of said tube for engaging the skin,
   an element disposed at said proximal region of said tube and configured to be non-lockingly engaged by a corresponding element of a tool to transmit torque from the tool to the tube, thereby to allow the tool to rotatably advance said tube into the skin using said threads, and
   a cap attached to said proximal region of said tube, said cap having a proximal surface that includes said element disposed at said proximal region of said tube.

2. The sleeve of claim 1 wherein said element of said tube includes a radially oriented slot disposed in a proximal surface of said tube and configured to receive a corresponding protrusion on the tool.

3. The sleeve of claim 2 wherein said element further comprises a plurality of circumferentially spaced, radially oriented slots disposed in said proximal surface of said tube and configured to receive a corresponding plurality of protrusions on the tool.

4. The sleeve of claim 1 wherein said proximal region of said tube includes a wall having a proximal end that surrounds said passage, said cap being attached to said tube by engagement with an interior portion of said proximal end of said wall.

5. The sleeve of claim 4 wherein said interior portion of said wall includes a notch therein, said cap including a resilient projection configured to be received by said notch to provide a snap fit between said cap and said tube.

6. The sleeve of claim 5 wherein said notch is disposed around the perimeter of said interior surface, said cap including a plurality of circumferentially spaced, resilient tabs each of which includes said projection.

7. The sleeve of claim 4 wherein said wall comprises a proximal extension of said tube and flares radially outwardly from said tube so that said proximal end of said wall is radially spaced from said exterior surface of said tube.

8. The sleeve of claim 7 wherein said proximal end of said wall is disposed proximally of a proximal end of said tube, said cap including an annular neck disposed adjacent said proximal end of said tube when said cap is attached to said tube.

9. The sleeve of claim 8 wherein said seal is captured between said annular neck of said cap and said proximal end of said tube.

10. The sleeve of claim 8 wherein said tube and said wall comprise an integral unit made from a single piece of plastic material.

11. The sleeve of claim 1 wherein said cap includes an opening through which the surgical instrument is inserted into said passage, and further comprising a plug that is insertable into said opening to close said passage at said proximal end.

12. The sleeve of claim 1 wherein said seal is annular and has an opening sized to receive the surgical instrument while maintaining surrounding portions of said seal in contact with the surgical instrument.

13. The sleeve of claim 12 wherein said seal comprises a silicone gasket.

14. A sleeve for a surgical instrument, comprising
   a hollow tube having a passage sized to accommodate the surgical instrument and extending between a proximal region of said tube and a distal region of said tube,
   threads disposed on an exterior surface of said tube for engaging the skin,
   a cap attached to said proximal region of said tube, said cap having a proximal surface that includes an element configured to be engaged by a corresponding element of a tool to transmit torque from the tool to the tube, thereby to allow the tool to rotatably advance said tube into the skin using said threads, and
   a seal for the surgical instrument secured within said passage by the attachment of said cap to said tube.

15. The sleeve of claim 14 wherein said cap and said proximal region of said tube include gripping projections.

16. A device for inserting a sleeve for a surgical instrument into a patient, said device comprising
   a handle,
   a post extending from an end of said handle and configured to receive the sleeve,
   an element disposed on said end of said handle and configured to non-lockingly engage a corresponding element on the sleeve to transmit torque from said handle to the sleeve, thereby to allow said handle to rotatably advance the sleeve into the skin,
   a stylet having a sharp tip for piercing the skin to create an opening for said post, said stylet being slidably disposed within said post and movable between a retracted position in which said tip is disposed within said post and an extended position in which said tip protrudes from said post,
   a pin coupled to said stylet and protruding through an opening in said handle, said pin being movable within said opening to move said stylet between said retracted position and said extended position.

17. The device of claim 16 further comprising
   a spring disposed within said handle and coupled to said stylet for biasing said stylet to the retracted position.

18. The device of claim 16 wherein said opening comprises a portion arranged along a longitudinal axis of said handle and a portion arranged transversely to said axis, said pin being movable within said axial portion to move said stylet between said retracted position and said extended position, said pin being displaceable into said transverse portion to maintain said stylet in said extended position.

19. Apparatus comprising:
   a sleeve for a surgical instrument, including
      a hollow tube having a passage sized to accommodate the surgical instrument and extending between a proximal region of said tube and a distal region of said tube,
      a seal for the surgical instrument disposed within said passage,
      threads disposed on an exterior surface of said tube for engaging the skin, and
      an element disposed at said proximal region; and
   a device for inserting said sleeve into a patient, including
      a handle and a post extending from an end of said handle and configured to receive the sleeve, and
      an element disposed on said end of said handle and configured to non-lockinqly engage said element on said sleeve to transmit torque from said handle to the tube, thereby to allow said handle to rotatably advance said sleeve into the skin using said threads.

20. The apparatus of claim 19 wherein said device further comprises
   a stylet having a sharp tip for piercing the skin to create an opening for said post, said stylet being slidably disposed within said post and movable between a retracted position in which said tip is disposed within said post and an extended position in which said tip protrudes from said post.

21. The apparatus of claim 19 wherein said seal is annular and has an opening sized to receive the surgical instrument while maintaining surrounding portions of said seal in contact with the surgical instrument.

22. A method for performing lipoplasty, comprising
   providing a sleeve that includes a hollow tube having a passage that extends between a proximal region of said tube and a distal region of said tube, threads disposed on an exterior surface of said tube for engaging the skin, and an element disposed at said proximal region, and
   providing a device for inserting said sleeve into a patient the includes a handle, a post extending from an end of said handle, a stylet having a sharp tip for piercing the skin to create an opening for said post, and an element disposed on said end of said handle and configured to non-lockinqly engage said element on said sleeve to transmit torque from said handle to said tube,
   inserting said sleeve onto said post so that said element disposed on said end of said handle engages said element on said sleeve,
   piercing the skin with said tip of said stylet, and
   rotating said handle to rotatably advance said sleeve into the skin using said threads.

23. The method of claim 22 further comprising disengaging said element disposed on said handle from said element disposed on said sleeve and withdrawing said post from said sleeve, and thereafter inserting a lipoplasty instrument through said passage and removing fat from the body with said instrument.

24. A sleeve for a surgical instrument, comprising a hollow tube having a passage sized to accommodate the surgical instrument and extending between a proximal region of said tube and a distal region of said tube, a seal for the surgical instrument disposed within said passage, threads disposed on an exterior surface of said tube for engaging the skin, an element disposed at said proximal region of said tube and configured to be engaged by a corresponding element of a tool to transmit torque from the tool to the tube, thereby to allow the tool to rotatably advance said tube into the skin using said threads, and a cap attached to said proximal region of said tube, said cap having a proximal surface that includes said element disposed at said proximal region of said tube.

25. The sleeve of claim 24 wherein said proximal region of said tube includes a wall having a proximal end that surrounds said passage, said cap being attached to said tube by engagement with an interior portion of said proximal end of said wall.

26. The sleeve of claim 25 wherein said interior portion of said wall includes a notch therein, said cap including a resilient projection configured to be received by said notch to provide a snap fit between said cap and said tube.

27. The sleeve of claim 26 wherein said notch is disposed around the perimeter of said interior surface, said cap including a plurality of circumferentially spaced, resilient tabs each of which includes said projection.

28. The sleeve of claim 25 wherein said wall comprises a proximal extension of said tube and flares radially outwardly from said tube so that said proximal end of said wall is radially spaced from said exterior surface of said tube.

29. The sleeve of claim 28 wherein said proximal end of said wall is disposed proximally of a proximal end of said tube, said cap including an annular neck disposed adjacent said proximal end of said tube when said cap is attached to said tube.

30. The sleeve of claim 29 wherein said seal is captured between said annular neck of said cap and said proximal end of said tube.

31. The sleeve of claim 29 wherein said tube and said wall comprise an integral unit made from a single piece of plastic material.

32. The sleeve of claim 24 wherein said cap includes an opening through which the surgical instrument is inserted into said passage, and further comprising a plug that is insertable into said opening to close said passage at said proximal end.

* * * * *